(12) United States Patent
Heideman

(10) Patent No.: US 8,974,650 B2
(45) Date of Patent: Mar. 10, 2015

(54) MICROFLUIDIC SYSTEM

(71) Applicant: Octrolix BV, Enschede (NL)

(72) Inventor: Rene Gerrit Heideman, Oldenzaal (NL)

(73) Assignee: Octrolix BV (NL)

(*) Notice: Subject to any disclaimer, the term of this patent is extended or adjusted under 35 U.S.C. 154(b) by 30 days.

(21) Appl. No.: 13/903,294

(22) Filed: May 28, 2013

(65) Prior Publication Data

US 2013/0256138 A1    Oct. 3, 2013

Related U.S. Application Data

(63) Continuation-in-part of application No. 12/172,740, filed on Jul. 14, 2008, now Pat. No. 8,454,811.

(51) Int. Cl.
| | |
|---|---|
| *B81B 7/00* | (2006.01) |
| *G01N 27/453* | (2006.01) |
| *B01L 3/00* | (2006.01) |
| *G01N 27/447* | (2006.01) |
| *B81B 1/00* | (2006.01) |
| *C03C 17/02* | (2006.01) |

(52) U.S. Cl.
CPC .... *B01L 3/502707* (2013.01); *G01N 27/44791* (2013.01); *B81B 1/00* (2013.01); *B01L 3/5027* (2013.01); *C03C 17/02* (2013.01); *G01N 27/44743* (2013.01); *B01L 3/569* (2013.01); *B01L 2300/12* (2013.01); *B01L 2400/0415* (2013.01)
USPC ............................ 204/451; 204/601; 422/502

(58) Field of Classification Search
USPC ................ 204/451, 601; 422/502–508; 137/3
See application file for complete search history.

(56) References Cited

FOREIGN PATENT DOCUMENTS

WO    WO 2008065868 A1  *  6/2008

* cited by examiner

*Primary Examiner* — J. Christopher Ball
(74) *Attorney, Agent, or Firm* — Kaplan Breyer Schwarz & Ottesen, LLP

(57) ABSTRACT

A method for forming a microfluidic channel with improved flow characteristics for one or more analytes is disclosed. A microfluidic channel having modified surfaces is formed in a glass layer or glass substrate. The glass surfaces of the microfluidic channel are modified by the addition of a layer of borophosphosilicate glass. The addition of the borophosphosilicate glass results in an improved flow velocity profile of the analyte. As a result, control over the position and movement of analytes within the solution is improved.

18 Claims, 4 Drawing Sheets

MICROFLUIDIC SYSTEM

CROSS REFERENCE TO RELATED APPLICATIONS

This case is a continuation-in-part of co-pending U.S. patent application Ser. No. 12/172,740, filed Jul. 14, 2008, which is incorporated by reference herein.

FIELD OF THE INVENTION

The present invention relates to microfluidics in general, and, more particularly, to the formation of microfluidic channels.

BACKGROUND OF THE INVENTION

Microfluidic systems offer potential advantage in applications such as chemical synthesis, distillation, and analysis. Such systems typically include one or more flow channels interconnected to chambers where minute volumes of fluids are introduced, extracted, separated, reacted, or dissociated into constituent components. In order for a microfluidic system to operate properly, the flow of analytes contained in the solutions that flow through the flow channels must be carefully controlled.

Often, a microfluidic system distributes buffered electrolyte containing one or more analytes through its flow channels by means of electroosmotic flow. Electroosmotic flow is achieved by means of an applied high electric field. In the presence of the electric field, ions are pulled through the flow channel. In some applications, such as capillary electrophoresis, the analytes separate within the flow channel due to differences in their electrophoretic mobility. As a result, separate chemicals or chemical compounds can be identified by the rate at which they flow through the flow channel. In some applications, the separated chemical compounds can be routed to different areas of the microfluidic system where they can take part in desired chemical reactions, be further separated, or be extracted from the system.

In many cases, the flow of analyte through the microfluidic system is not well controlled due to physical and electrical effects associated with the channel walls. These effects can create uncertainty in the detection of the analyte or errors in the introduction of an analyte into a chemical reaction.

SUMMARY OF THE INVENTION

The present invention provides a microfluidic channel that avoids some of the costs and disadvantages of the prior art. In particular, the present invention provides a microfluidic channel that exhibits analyte flow characteristics that are improved over prior art microfluidic channels. Embodiments of the present invention are well suited to applications such as lab-on-a-chip, microreactors, analytic systems, capillary electrophoresis, and the like.

Conventional microfluidic channels are fabricated in and from materials that are substantially chemically inert to solutions of interest. Fused silica is often used as the material of choice in such systems. Unfortunately, for many analytes, fused silica exhibits poor flow characteristics. In particular, fused silica can induce a large degree of flow velocity variation within an analyte plug, which can cause the analyte plug to "smear out" as it progresses through the microchannel. Such variation is typically due to the physical structure of the channel walls and electrical interactions between the exposed surfaces of the fused silica channel walls and the analyte.

Like the prior art, some embodiments of the present invention utilize fused silica as a base material in which microfluidic channels are formed. In contrast to the prior art, however, the present invention treats the surfaces of the fused silica channel walls to mitigate surface interactions between these surfaces and the solution. In particular, in some embodiments a layer of borophosphosilicate glass is disposed on the exposed surfaces of the microfluidic channels. As compared to fused silica, the surface roughness of the borophosphosilicate layers is lower. In addition, in some embodiments, borophosphosilicate glass provides a higher electrokinetic potential that enables at least some analytes to maintain a well-formed analyte plug while traveling the length of a flow channel.

Borophosphosilicate microchannels are known in the prior art. Specifically, Callender, et al., have disclosed borophosphosilicate glass microchannels in publications including "Microchannel Arrays in Borophosphosilicate Glass for Photonic Device and Optical Sensor Applications," Materials Research Symposium Proceedings, Vol. 872, pp. J16.3.1-J16.3.6 (2005). Borophosphosilicate microchannels such as these, however, are limited to a circular or elliptical cross-sectional shape within a narrow size range due to the manner in which they are formed. They are formed by depositing a thick layer of borophosphosilicate glass with an intentional void. The layer is then annealed to induce the void to take on an elliptical or circular cross-sectional shape.

In contrast to what is disclosed by Callender, the present invention enables formation of microfluidic channels that have nearly any desired cross-sectional shape. The flow characteristics of a microfluidic channel are inexorably tied to the cross-sectional shape of the channel itself. As a result, the present invention enables a greater flexibility in channel design and microsystem functionality.

Finally, in some embodiments, the presence of borophosphosilicate glass enables the use of thermo-anodic bonding to join a channel plate substrate and a cover plate to form an enclosed microfluidic channel.

A microfluidic system that is dimensioned and arranged to convey a first solution, the first solution comprising an analyte, wherein the microfluidic system comprises: a first glass substrate including a first layer that comprises a trench having a first surface comprising a first material, the first material and the first solution being characterized by a first electrokinetic potential having a first magnitude; a second layer comprising a second surface of a second material, wherein the second layer is disposed on and in contact with the first surface, the second material and the first solution being characterized by a second electrokinetic potential having a second magnitude that is greater than the first magnitude; and a second substrate, wherein the second substrate comprises a third surface, and wherein the third surface comprises the second material, the first substrate and the second substrate being physically coupled such that the third surface and the trench collectively define a channel whose cross-section has a closed perimeter comprising at least one straight portion.

DETAILED DESCRIPTION

In the illustrative embodiment of the present invention, a capillary electrophoresis (CE) system based on surface-modified microfluidic channels is used to detect the presence of an analyte in a solution. A CE system is one example of a microfluidic system for which the present invention is suitable. Precise detection of the presence and/or concentration of an analyte at a location in a microfluidics system is important in many microfluidic applications, such as lab-on-a-chip, microreactors, analytic systems, capillary electrophoresis, and the like.

Figure 1:
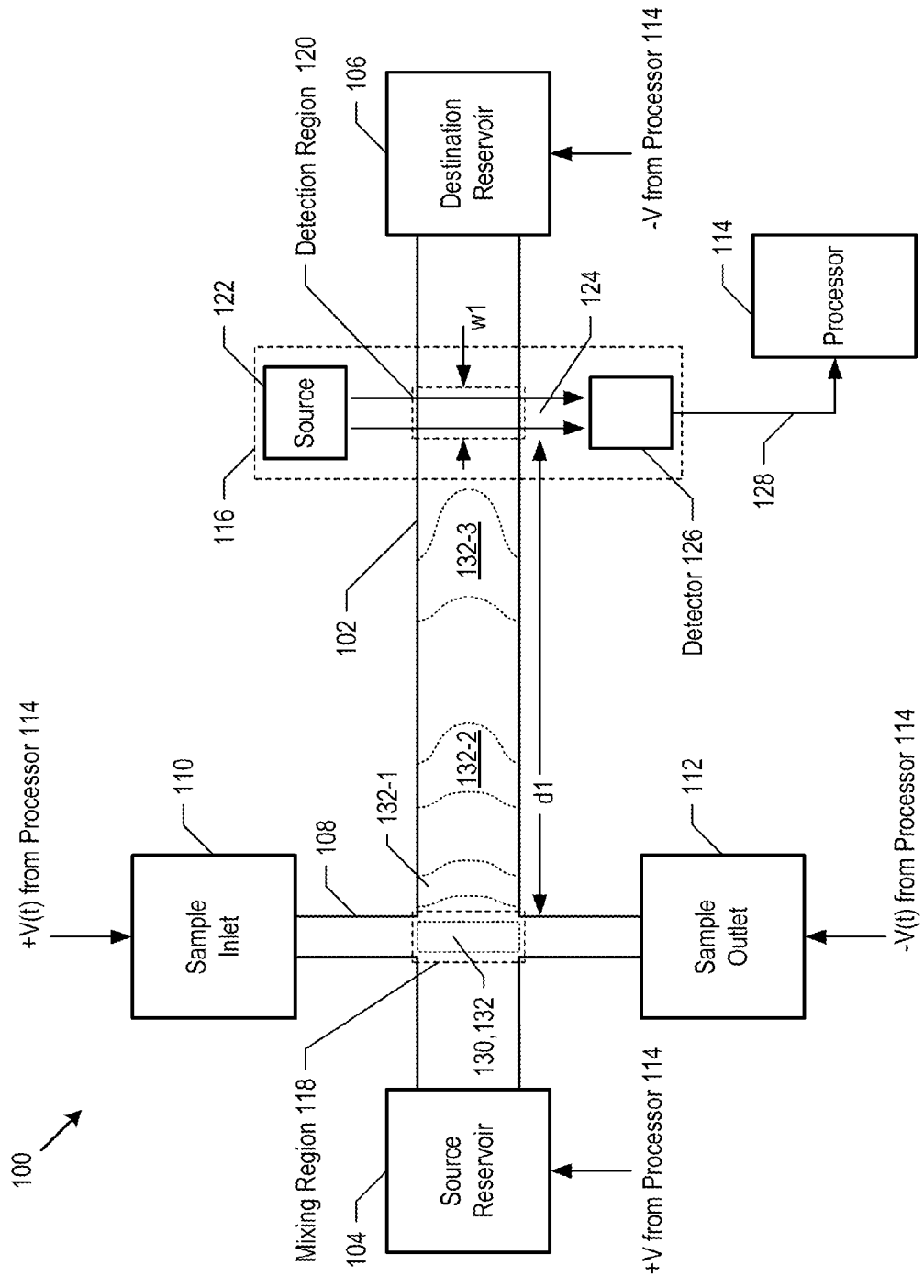
FIG. 1 depicts a schematic diagram of details of a capillary electrophoresis system (hereinafter, CE system) in accordance with the prior art.

FIG. 1 depicts a schematic diagram of details of a capillary electrophoresis system (hereinafter, CE system) in accordance with the prior art. CE system 100 comprises flow channel 102, source reservoir 104, destination reservoir 106, sample channel 108, sample inlet 110, sample outlet 112, processor 114, and sensor 116.

Capillary electrophoresis is a well-known technique for analyzing samples of chemicals, cells, and biological matter. In operation, a buffer solution flows through flow channel 102 from source reservoir 104 to destination reservoir 106. Processor 114 applies a steady-state high voltage, V, typically in the range of 1-5 kilovolts, between source reservoir 104 and destination reservoir 106. This high voltage induces electro-osmotic flow of the buffer solution along flow channel 102 from source reservoir 104 to destination reservoir 106. In some CE systems, flow of buffer solution through flow channel 102 is induced by applying a pressure differential between source reservoir 104 to destination reservoir 106.

Figure 2:
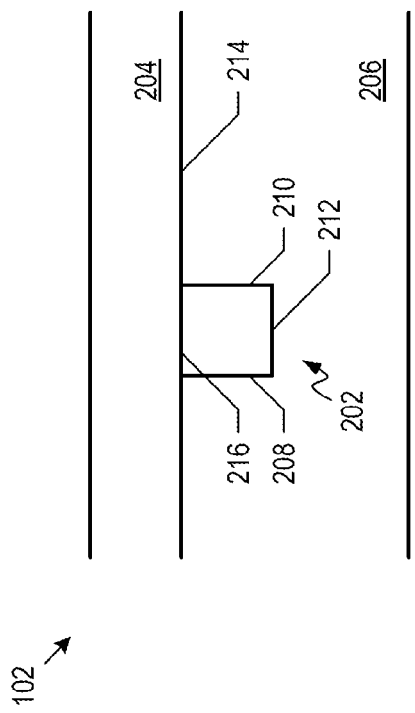
FIG. 2 depicts a cross-sectional view of flow channel 102, in accordance with the prior art.

FIG. 2 depicts a cross-sectional view of flow channel 102, in accordance with the prior art. Flow channel 102 comprises trench 202 and cover plate 204. Trench 202 is formed in substrate 206 and comprises sidewalls 208 and 210, and bottom 212.

Substrate 206 is a wafer of fused silica that has a thickness of approximately 500 microns. Trench 202 is etched into surface 214 of substrate 206 using conventional etching techniques to form sidewalls 208 and 210 and bottom 212.

Cover plate 204 is a wafer of fused silica that has a thickness of approximately 500 microns. During fabrication of CE system 100, surface 216 of cover plate 204 is attached to surface 214 of substrate 206 using fusion bonding. Openings in cover plate 204 that enable access to source reservoir 104, destination reservoir 106, sample inlet 110 and sample outlet 112 are formed using conventional techniques, such as sand blasting, wet etching or reactive ion etching.

Trench 202 is an open-topped trench having a substantially square cross-section of approximately 25-200 microns per side. The aspect ratio of trench 202 is dictated by its application and can vary over a wide range.

At time t(0), processor 114 applies a voltage difference $\Delta V(t)$ between sample inlet 110 and sample outlet 112. This applied voltage difference induces loading of sample solution in the interjacent channel, resulting in a sample plug 130) to be injected into the separation channel at region 118. Typically, sample plug 130 contains a mixture of several analytes.

As sample plug 130 flows through the length, d1, of flow channel 102, the analyte compounds of the sample solution become separated. The analytes separate because each analyte travels through flow channel 102 at a rate that is based on its individual electrophoretic mobility. An individual analyte's electrophoretic mobility is dependent on its net ionic charge and its hydrodynamic radius. An example of one analyte constituent (i.e., analyte plug 132) is depicted in FIG. 1 at three different times and locations along flow channel 102.

Detector 116 is an optical detector for detecting the presence of an analyte in the buffer solution at detection region 120. Detector 116 includes light source 122 and photodetector 126. Light source 122 emits a substantially collimated beam of light that passes through flow channel 102 at detection region 120. The width of the collimated beam of light determines the width, w1, of detection region 120. In some CE systems, simple visual inspection is used to detect the presence of an analyte. In other CE systems, non-optical detection means, such as electrical conductivity sensors, are used to detect an analyte.

Detector 116 generates a signal in response to a change in the optical characteristics of the solution in detection region 120, wherein the change is due to the presence of an analyte in the buffer solution. Prior to any of the constituent analytes of the sample solution reaching it, detection region 120 contains only pure buffer solution. As a result, optical signal 124 is received by photodetector 126 at a steady-state intensity. The intensity of optical signal at photodetector 126 is based on the absorption coefficient and refractive index of the pure buffer solution. Prior to the arrival of an analyte at detection region 120, therefore, photodetector 126 provides a steady-state output signal 128 to processor 114.

At time t(1), a first analyte reaches detection region 120, which causes a change in the absorption coefficient and/or refractive index of the solution. This causes a change in the optical power received by photodetector 126 and a corresponding change in output signal 128. As the first analyte clears detection region 120, output signal 128 returns to its prior steady-state level. This process repeats at time t(2) for a second analyte, time t(3) for a third analyte, and so on.

Processor 114 receives output signal 128 and determines the time between sample injection, t(0) and the time each analyte was detected in detection region 120 (i.e., t(1), t(2), etc.). Processor 114 then derives an identity for each analyte based on this time differential and the distance, d1, between mixing region 118 and detection region 120 (i.e., t(1)–t(0), t(2)–t(0), etc.), and the geometry of the flow channel.

Neglecting sidewall effects, the velocity of an analyte through flow channel 102 is a function of electrophoretic mobility, $\upsilon_p$, electroosmotic mobility, $\mu_p$, and the strength of the applied electric field, E, and is given as $v_a=(\upsilon_p+\mu_p)E$. The electrophoretic mobility of an analyte particle, at a given buffer solution pH, is given by:

$$\upsilon_p = \frac{z}{6\pi\eta r},$$

where z is the net charge of the analyte particle, $\eta$ is the viscosity of the buffer solution, and r is the Stokes radius of the analyte particle, which is inversely proportional to the analyte's diffusion coefficient. Typically, electrophoretic mobility is determined experimentally.

Electroosmotic mobility is given by:

$$\mu_p = \frac{\varepsilon \zeta}{\eta},$$

where $\zeta$ is the electrokinetic potential (a.k.a. "zeta potential") of the channel sidewall and $\varepsilon$ is the relative permittivity of the solution.

Unfortunately, interactions between the analyte and the surface of the microfluidic channel impact the flow of each analyte and cause each analyte plug to "smear" as it travels the length, d1, of flow channel 102, as depicted in FIG. 1 as analyte plugs 132-1, 132-2, and 132-3. Analyte plugs 132-1, 132-2, and 132-3 represent analyte plug 132 at three different times and positions within flow channel 102. The deformation of plug 132 results in part from article/surface interactions that are due to a "drag" on the analyte that occurs near the flow channel wall. As a result, analyte plug 132 becomes increasingly elongated as it progresses along flow channel 102.

Analyte plug 132-1 represents the shape of the sample immediately after its introduction into flow channel 102. At this point in time, the analyte plug is contained within a region that is approximately the size of mixing region 108.

Analyte plug 132-2 represents the shape of the analyte plug after it has traveled roughly one-third of the length of d1. As depicted, the rate at which the analyte near the channel walls travel is slower than that of the analyte nearer the center of the flow channel. As a result, analyte plug 132-2 has become a distorted version of analyte plug 132-1. In addition, the concentration of analyte within analyte plug 132-2 drops as the fixed amount of analyte is spread throughout a larger volume of buffer solution.

Analyte plug 132-3 represents the shape of the analyte plug after it has traveled nearly the entire length of flow channel 102. As depicted, analyte plug 132-3 is an even more distorted version of analyte plug 132-2, and has a commensurately lower local concentration.

As a result of this smearing out of the analyte plug, accurate detection of the analyte at detection region 120 becomes more difficult for a number of reasons. First, the size of the analyte plug can become larger than the size of the detection region. This can create uncertainty as to the precise position of the analyte plug with respect to the detection region.

Second, as the analyte plug smears and becomes longer, the distribution of analyte within the plug becomes more Gaussian. As a result, the entry of the analyte plug into the detection region results in a slower change in the measured property used to detect the analyte's presence. In similar fashion, as the analyte plug exits the detection region, a slower reverse of the change in the measured property occurs. As a result, presence of the analyte within the detection region is not marked by a sharp boundary that is easily detectable.

Third, since the finite amount of analyte is spread over a longer plug length, its total concentration level is reduced. As a result, changes in the physical properties useful for detection of the analyte (e.g., refractive index, electrical conductivity, etc.) can become attenuated and harder to detect.

Figure 3:
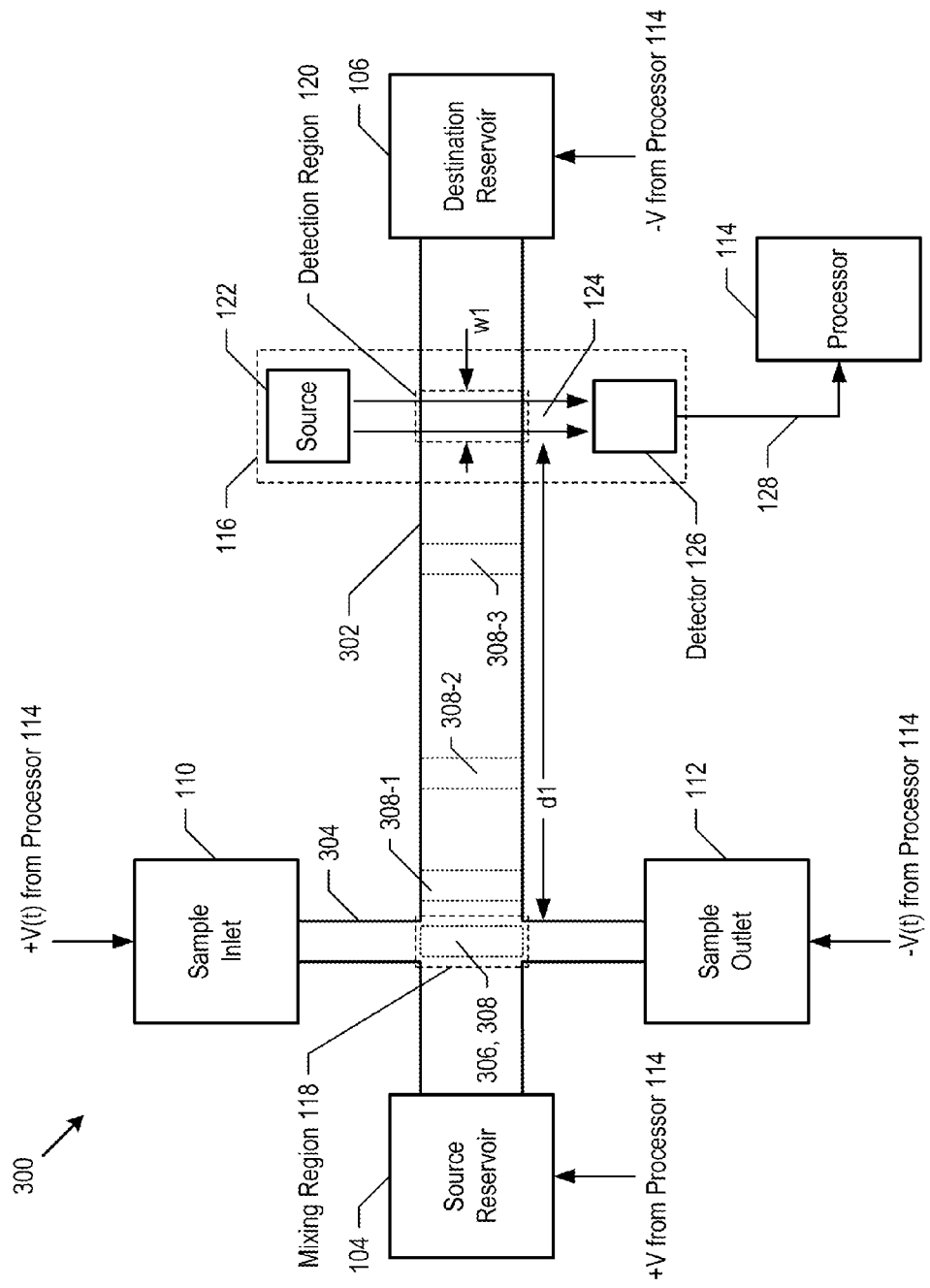
FIG. 3 depicts a schematic diagram of details of a CE system in accordance with an illustrative embodiment of the present invention.

FIG. 3 depicts a schematic diagram of details of a CE system in accordance with an illustrative embodiment of the present invention. CE system 300 comprises flow channel 302, source reservoir 104, destination reservoir 106, sample channel 304, sample inlet 110, sample outlet 112, processor 114, and sensor 116.

The operation of CE system 300 is analogous to the operation of CE system 100. The flow of analyte plug 308 along length d1 of flow channel 304, however, proceeds substantially free of the deformation that characterizes the flow of analyte plug 132 through flow channel 102, as described above and with respect to FIG. 1. As described above for analyte plug 132, FIG. 3 depicts analyte plug 308 at three different positions and times—denoted as 308-1, 308-2, and 308-3. Analyte plug 308-1 represents the shape of analyte plug 308 immediately after is introduction into flow channel 102, analyte plug 308-2 represents the shape of analyte plug 308 after it has traveled roughly one-third of the length of d1, and analyte plug 308-3 represents the shape of analyte plug 308 after it has traveled nearly the entire length of flow channel 102.

Figure 4:
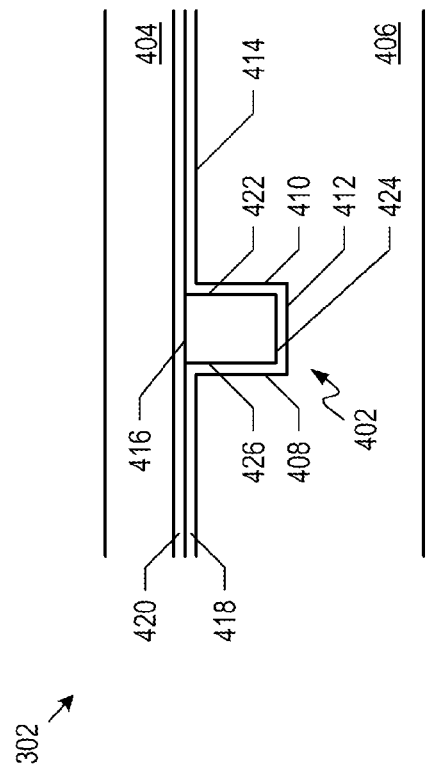
FIG. 4 depicts a cross-sectional view of flow channel 302, in accordance with the illustrative embodiment of the present invention.

FIG. 4 depicts a cross-sectional view of flow channel 302, in accordance with the illustrative embodiment of the present invention. Flow channel 302 comprises trench 402 and cover plate 404. Trench 402 is formed in substrate 406 and comprises sidewalls 408 and 410, and bottom 412.

It should be noted that microfluidic channels formed in borophosphosilicate are known in the prior art. For example, Callender, et al., have disclosed borophosphosilicate glass microchannels in publications including "Microchannel Arrays in Borophosphosilicate Glass for Photonic Device and Optical Sensor Applications," *Materials Research Symposium Proceedings*, Vol. 872, pp. J16.3.1-J16.3.6 (2005). Such borophosphosilicate microfluidic channels, however, are limited to a circular or elliptical cross-sectional shape within a narrow size range. This limitation arises from the manner in which they are formed. Specifically, they are formed by depositing a thick layer of borophosphosilicate glass in a manner that produces an intentional void in the middle of the borophosphosilicate layer. This layer is then annealed to reflow the borophosphosilicate material, thereby inducing the void to form into an elliptical or circular cross-sectional shape.

In contrast to the teachings of Callender, the present invention enables formation of microfluidic channel with any desired cross-sectional shape. As a result, the present invention enables design of a microfluidic channel with nearly any desirable set of geometrically determined flow characteristics.

Figure 5:
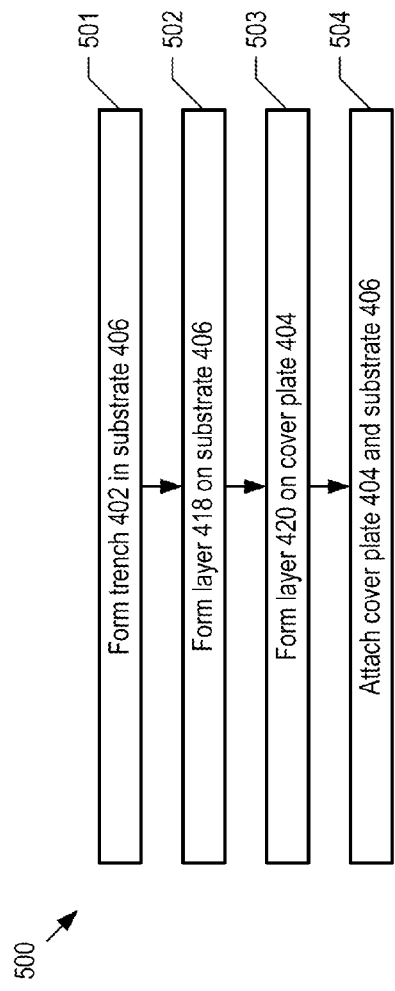
FIG. 5 depicts a method for forming a microfluidic channel in accordance with the illustrative embodiment of the present invention.

FIG. 5 depicts a method for forming a microfluidic channel in accordance with the illustrative embodiment of the present invention. Method 500 is described herein with continuing reference to FIGS. 3 and 4.

Method 500 begins with operation 501, wherein trench 402 is formed in substrate 406. Substrate 406 is a 100 mm-diameter wafer of fused silica and has a thickness of approximately 500 microns. In some embodiments, substrate 406 comprises a material other than fused silica. Glasses suitable for use in substrate 406 include, without limitation, fused silica, Pyrex, float glass, fused quartz, quartz, non-oxide glasses (e.g., fluoride glasses, etc.), crown glass, and the like. In some embodiments, substrate 406 is a material other than fused silica and includes a layer of fused silica, or other suitable glass, disposed on at least one surface, wherein trench 402 is formed in this layer.

Trench 402 is formed using conventional methods, such as DRIE, reactive ion etching, wet etching, single-point diamond machining, sand blasting, or laser-assisted etching. Trench 402 has a substantially u-shape with feature sizes within the range of approximately 25-200 microns per side. In some embodiments, trench 402 has a different shape, such as an open-topped rectangle, triangle, trapezoid, semicircle, semi-oval, and the like.

At operation 502, layer 418 is deposited on substrate 406. Layer 418 is a layer of borophosphosilicate glass (BPSG) having a thickness within the range of approximately 10 nanometers (nm) to approximately 5 microns. In some embodiments, the thickness of layer 418 is approximately 1 micron. Layer 418 is deposited using low-pressure chemical vapor deposition (LPCVD) to form a conformal coating. As a result, layer 418 is disposed, with substantially uniform thickness, on surfaces 414, 408, 410, and 412 of substrate 406. By virtue of the deposition of layer 418, the interior surface of trench 402 comprises surfaces 422, 424, and 426, which are all BPSG surfaces. The formation of layer 420 results in a smoothing of the surface to which the analyte plug is exposed. As a result, the analyte plug is less susceptible to smearing out as it flows along the microchannel.

At operation 503, layer 420 is formed on cap layer 404. Layer 420 is a layer of BPSG having a thickness within the range of approximately 10 nm to approximately 5 microns. Layer 420 comprises surface 416. In some embodiments, the thickness of layer 420 is approximately 1 micron. In some embodiments, cap layer 404 is a wafer of fused silica having a thickness of approximately 500 microns. In some embodiments, cap layer 404 comprises a material other than fused silica. Glasses suitable for use in cap layer 404 include, without limitation, fused silica, Pyrex (i.e., low-thermal-expansion borosilicate glass), float glass (e.g., borofloat glass [i.e., floated borosilicate glass], etc.), crown glass, fused quartz, quartz, and the like.

Although the illustrative embodiment comprises layers 418 and 420 that each have a thickness of approximately 1 micron, it will be clear to one skilled in the art, after reading this specification, how to specify, make, and use alternative embodiments of the present invention wherein at least one of layers 418 and 420 has a different thickness. It will also be clear, after reading this specification, how to make and use alternative embodiments of the present invention wherein a portion of at least one of layers 418 and 420 is removed using conventional techniques.

At operation 504, cover plate 404 is attached to substrate 406 by means of fusion bonding. Once cover plate 404 and substrate 406 are attached, flow channel 302 is fully formed and has an interior surface that is exclusively BPSG. As a result, the electrokinetic potential of the interior surfaces of flow channel 302 is well matched to that of the analyte included in analyte plug 308. In some embodiments, cover plate 404 is attached to substrate 406 via another conventional wafer bonding process, such as thermo-anodic bonding.

Figure 6:
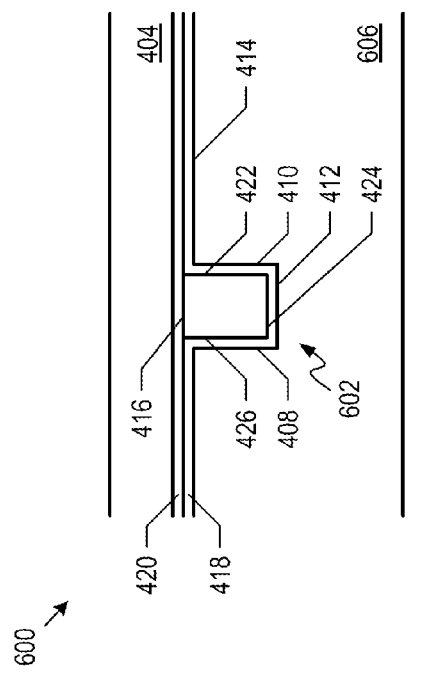
FIG. 6 depicts a cross-sectional view of a flow channel in accordance with a first alternative embodiment of the present invention.

FIG. 6 depicts a cross-sectional view of a flow channel in accordance with a first alternative embodiment of the present invention. Flow channel 600 comprises trench 602 and cover plate 404. Trench 602 is formed in layer 606, which is disposed on base substrate 604. Trench 602 comprises sidewalls 408 and 410, and bottom 412.

Trench 602 is analogous to trench 402 described above and with respect to FIG. 4.

Base substrate 604 is a substrate suitable for use in a planar processing fabrication process. Materials suitable for use in the base substrate include, without limitation, semiconductors (e.g., silicon, III-V semiconductors, II-VI semiconductors, germanium, silicon carbide, etc.), ceramics (e.g., alumina, etc.), composite materials, metals, glasses, and the like.

Layer 606 is a layer of glass disposed on base substrate 604. Materials suitable for use in layer 606 include, without limitation, thermally grown silicon dioxide, deposited oxide, tetraethyl orthosilicate (TEOS), etc.), fused silica, Pyrex, float glass, spin-on glasses, and the like.

In some embodiments, layer 606 is a layer formed on base substrate 604 via a conventional deposition process, such as plasma-enhanced-chemical-vapor-deposition (PECVD), low-pressure-chemical-vapor-deposited (LPCVD), sputter deposition, and the like. Materials suitable for deposition on base substrate 604 include, without limitation, PECVD-deposited glasses (e.g., oxides, oxynitrides, silicon monoxide, etc.), LPCVD-deposited glasses (e.g., oxides, oxynitrides, silicon monoxide, TEOS, non-oxide glasses, etc.), In some embodiments, layer 606 is a layer of glass that is prefabricated to a desired thickness and bonded to base substrate 604 using conventional wafer bonding methods. In some embodiments, the thickness of layer 606 is controlled after it is disposed on base substrate 604.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A microfluidic system that is dimensioned and arranged to convey a first solution, the first solution comprising an analyte, wherein the microfluidic system comprises:
   a first glass substrate including a first layer that comprises a trench having a first surface comprising a first material, the first material and the first solution being characterized by a first electrokinetic potential having a first magnitude, wherein the first material comprises a material selected from the group consisting of low-thermal-expansion borosilicate glass, floated borosilicate glass, borosilicate glass, TEOS, thermally grown silicon dioxide, PECVD oxide, and LPCVD oxide;
   a second layer comprising a second surface of a second material comprising borophosphosilicate glass, wherein the second layer is disposed on and in contact with the first surface, the second material and the first solution being characterized by a second electrokinetic potential having a second magnitude that is greater than the first magnitude; and
   a second substrate, wherein the second substrate comprises a third surface, and wherein the third surface comprises the second material, the first substrate and the second substrate being physically coupled such that the third surface and the trench collectively define a channel whose cross-section has a closed perimeter comprising at least one straight portion.

2. The microfluidic system of claim 1 further comprising a detector for detecting the analyte, wherein the detector and the trench are operatively coupled.

3. The microfluidic system of claim 1 wherein the closed cross-section has a substantially rectangular shape.

4. The microfluidic system of claim 1 wherein the closed cross-section has a substantially triangular shape.

5. A method for forming a microfluidic system for conveying a first solution comprising an analyte, wherein the method comprises:
   forming a trench in a first substrate comprising a first glass, wherein the trench has a first surface comprising the first glass, and wherein the first glass and the first solution are characterized by a first electrokinetic potential having a first magnitude, wherein the first glass comprises a material selected from the group consisting of low-thermal-expansion borosilicate glass, floated borosilicate glass, borosilicate glass, TEOS, thermally grown silicon dioxide, PECVD oxide, and LPCVD oxide;

forming a first layer of borophosphosilicate glass on the first substrate to form a second surface that is disposed on the first surface, wherein borophosphosilicate glass and the first solution are characterized by a second electrokinetic potential having a second magnitude that is greater than the first magnitude;

providing a second substrate, wherein the second substrate comprises a third surface comprising the borophosphosilicate glass; and attaching the first substrate and the second substrate such that they collectively define a microfluidic channel whose cross-section has a closed perimeter comprising at least one straight portion.

6. The method of claim 5 wherein the second substrate and the first substrate are attached using thermo-anodic bonding.

7. The method of claim 5 wherein the second substrate and the first substrate are attached using fusion bonding.

8. The method of claim 5 further comprising:
providing the first substrate, wherein the first substrate comprises a second layer that comprises the first glass, and wherein the trench is formed in the second layer;
wherein the first layer is formed by disposing borophosphosilicate glass on the second layer.

9. The method of claim 5 wherein the trench is formed such that the first surface comprises sidewalls and a bottom, and wherein the first layer is disposed as a conformal coating on the sidewalls and the bottom.

10. A method for forming a microfluidic system for conveying a first solution comprising an analyte, wherein the method comprises:
providing a substrate having a first layer, the substrate comprising a first glass selected from the group consisting of low-thermal-expansion borosilicate glass, floated borosilicate glass, borosilicate glass, TEOS, thermally grown silicon dioxide, PECVD oxide, and LPCVD oxide;
forming a trench in a first layer, wherein the trench comprises a first surface comprising a first material that is a second glass selected from the group consisting of low-thermal-expansion borosilicate glass, floated borosilicate glass, borosilicate glass, TEOS, thermally grown silicon dioxide, PECVD oxide, and LPCVD oxide, and wherein the first material and the first solution are characterized by a first electrokinetic potential having a first magnitude;

forming a second layer on the first surface to form a second surface, wherein the second surface comprises a second material, and wherein the second material and the first solution are characterized by a second electrokinetic potential that is greater than the first magnitude;

providing a cover plate, wherein the cover plate comprises a third surface comprising the second material; and attaching the cover plate and the first layer to form a conduit having an inner surface that comprises the second surface and the third surface, wherein the conduit has a cross-section characterized by a closed shape having at least one straight portion.

11. The method of claim 10 further comprising forming the second layer by disposing a layer of borophosphosilicate glass on the first surface.

12. The method of claim 11 wherein the second layer is formed such that the second layer is disposed on a top surface of the first layer, and wherein the cover plate and the first layer are attached by bonding the second layer and the third layer using thermo-anodic bonding.

13. The method of claim 11 wherein the second layer is formed such that the second layer is disposed on a top surface of the first layer, and wherein the cover plate and the first layer are attached by bonding the second layer and the third layer using fusion bonding.

14. The method of claim 10 wherein the cover plate comprises a first substrate comprising a second glass, and wherein the method further comprises forming the third layer by depositing borophosphosilicate glass on the first substrate.

15. The method of claim 10 wherein the inner surface is substantially uniformly borophosphosilicate glass.

16. The method of claim 10 wherein the cross-section has a substantially rectangular shape.

17. The method of claim 10 wherein the cross-section has a substantially triangular shape.

18. The method of claim 10, wherein the first glass and the second glass are the same glass.

* * * * *